(12) United States Patent
Power et al.

(10) Patent No.: US 10,546,482 B2
(45) Date of Patent: Jan. 28, 2020

(54) DEVICE HAVING POST-MEAL TEST-TIME ALARM

(71) Applicant: ASCENSIA DIABETES CARE HOLDINGS AG, Basel (CH)

(72) Inventors: Barry D. Power, Elkhart, IN (US); Jeffrey A. Culver, Sylvania, OH (US)

(73) Assignee: ASCENSIA DIABETES CARE HOLDINGS AG, Basel (CH)

( * ) Notice: Subject to any disclaimer, the term of this patent is extended or adjusted under 35 U.S.C. 154(b) by 0 days.

(21) Appl. No.: 16/250,761

(22) Filed: Jan. 17, 2019

(65) Prior Publication Data

US 2019/0156651 A1    May 23, 2019

Related U.S. Application Data

(63) Continuation of application No. 15/210,307, filed on Jul. 14, 2016, now Pat. No. 10,223,893, which is a continuation of application No. 11/989,815, filed as application No. PCT/US2006/030594 on Aug. 4, 2006, now abandoned.

(Continued)

(51) Int. Cl.
| | | |
|---|---|---|
| *G01N 1/00* | (2006.01) | |
| *G08B 21/24* | (2006.01) | |
| *A61B 5/145* | (2006.01) | |
| *A61B 5/00* | (2006.01) | |
| *G06F 19/00* | (2018.01) | |
| *G16H 40/63* | (2018.01) | |
| *G16H 20/10* | (2018.01) | |

(52) U.S. Cl.
CPC .......... *G08B 21/24* (2013.01); *A61B 5/14532* (2013.01); *A61B 5/14546* (2013.01); *A61B 5/7475* (2013.01); *G06F 19/3456* (2013.01); *G16H 20/10* (2018.01); *G16H 40/63* (2018.01)

(58) Field of Classification Search
CPC ....................................................... G01N 1/00
See application file for complete search history.

(56) References Cited

U.S. PATENT DOCUMENTS

| 4,686,624 A | 8/1987 | Blum |
| 5,673,691 A | 10/1997 | Abrams |

(Continued)

FOREIGN PATENT DOCUMENTS

| JP | 2001-221803 | 8/2001 |
| JP | 2003-204941 | 7/2003 |

(Continued)

OTHER PUBLICATIONS

International Search Report corresponding to International Patent Application No. PCT/US2006/030594, European Patent Office, dated Nov. 30, 2006 (5 pages).

(Continued)

*Primary Examiner* — Jyoti Nagpaul
(74) *Attorney, Agent, or Firm* — Nixon Peabody LLP

(57) ABSTRACT

A method for using a meter and a meter (10) adapted to determine an analyte concentration reading, the meter comprising a display (12) adapted to display information to a user of the meter, the display including information directed to a post-meal test-time alarm (22") that is adapted to remind the user to obtain a post-meal analyte concentration reading, and at least one user input mechanism (15) adapted to allow the user to activate the post-meal test-time alarm.

19 Claims, 1 Drawing Sheet

Related U.S. Application Data

(60) Provisional application No. 60/705,957, filed on Aug. 5, 2005.

(56) References Cited

U.S. PATENT DOCUMENTS

| | | |
|---|---|---|
| 5,822,715 A | 10/1998 | Worthington |
| 6,167,362 A | 12/2000 | Brown |
| 6,246,966 B1 | 6/2001 | Perry |
| 6,574,425 B1 | 6/2003 | Weiss |
| 6,925,393 B1 | 8/2005 | Kalatz |
| 7,399,277 B2 | 7/2008 | Saidara |
| 2002/0087054 A1 | 7/2002 | Lin |
| 2004/0015102 A1 | 1/2004 | Cummings |
| 2004/0059201 A1 | 3/2004 | Ginsberg |
| 2005/0038332 A1 | 2/2005 | Saidara |
| 2005/0038674 A1 | 2/2005 | Braig |
| 2006/0089540 A1 | 4/2006 | Meissner |
| 2007/0016170 A1 | 1/2007 | Kovelman |

FOREIGN PATENT DOCUMENTS

| | | |
|---|---|---|
| TW | 537878 | 6/2003 |
| TW | 592664 | 6/2004 |

OTHER PUBLICATIONS

Written Opinion corresponding to International Patent Application No. PCT/US2006/030594, European Patent Office, dated Nov. 30, 2006 (5 pages).

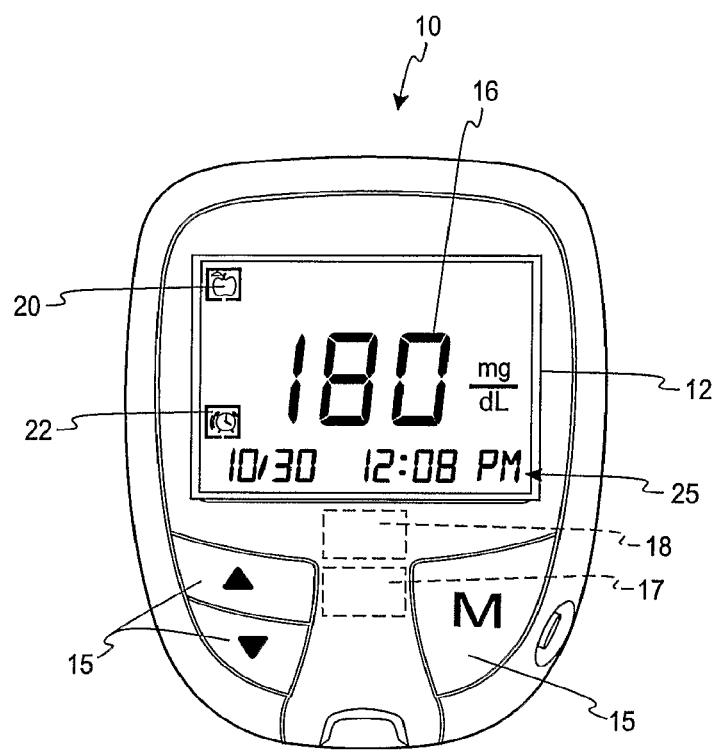

DEVICE HAVING POST-MEAL TEST-TIME ALARM

CROSS-REFERENCE TO RELATED APPLICATIONS

This application is a continuation of U.S. application Ser. No. 15/210,307 filed Jul. 14, 2006, which is a continuation of U.S. application Ser. No. 11/989,815 filed Jan. 30, 2008, which is a 371 of PCT/US06/30594 filed Aug. 4, 2006, and which claims priority to U.S. Provisional Application No. 60/705,957, filed on Aug. 5, 2005, all of which are hereby incorporated by reference in their entireties.

FIELD OF THE INVENTION

The present invention relates generally to meters and methods of using the same, and more particularly, to a meter having a post-meal test-time alarm for notifying a user when it is time to measure an analyte concentration following a meal.

BACKGROUND OF THE INVENTION

The quantitative determination of analytes in body fluids is of great importance in the diagnoses and maintenance of certain physiological abnormalities. For example, lactate, cholesterol, bilirubin and glucose should be monitored in certain individuals. In particular, determining glucose in body fluids is important to diabetic individuals who must frequently check the glucose concentration in their body fluids to regulate the glucose intake in their diets.

Diabetic individuals often test their blood glucose levels via a blood glucose meter. Health care professionals recognize that it is particularly important for a person with diabetes to test his or her blood glucose level about two hours after a meal. This length of time after a meal represents the time frame when blood glucose levels typically spike and can cause the most harm. Thus, it would be desirable to have a meter that provides a reminder or stimulus to the user to check his or her blood glucose level about two hours after a meal.

SUMMARY OF THE INVENTION

A meter is disclosed according to one embodiment of the present invention. The meter is adapted to determine an analyte concentration reading. The meter includes a display adapted to display information to a user of the meter. The display includes information directed to a post-meal test-time alarm that is adapted to remind the user to obtain a post-meal analyte concentration reading. The meter includes at least one user input mechanism adapted to allow the user to activate the post-meal test-time alarm.

A method for using a meter adapted to determine an analyte concentration reading is disclosed according to one embodiment of the present invention. The meter has a display adapted to display information to a user. The method includes the acts of displaying information relating to a post-meal test-time alarm, activating the post-meal test-time alarm via an input mechanism, and sounding the post-meal test-time alarm after a predetermined amount of time to remind the user to obtain a post-meal analyte concentration reading.

The above summary of the present invention is not intended to represent each embodiment, or every aspect, of the present invention. Additional features and benefits of the present invention are apparent from the detailed description, and FIGURES set forth below.

BRIEF DESCRIPTION OF THE DRAWING

FIG. 1 is a front side view of a meter having a post-meal test-time alarm feature according to one embodiment of the present invention.

DESCRIPTION OF ILLUSTRATED EMBODIMENTS

The present invention is directed to a meter that is adapted to determine an analyte concentration in a body fluid sample which is collected with a lancing device. Examples of the types of analytes which may be collected include glucose, lipid profiles (e.g., cholesterol, triglycerides, LDL and HDL), microalbumin, hemoglobin A1C, fructose, lactate, or bilirubin. It is contemplated that other analyte concentrations may also be determined. The analytes may be in, for example, a whole blood sample, a blood serum sample, a blood plasma sample, other body fluids like ISF (interstitial fluid) and urine, and non-body fluids. As used within this application, the term "concentration" refers to an analyte concentration, activity (e.g., enzymes and electrolytes), titers (e.g., antibodies), or any other measure concentration used to measure the desired analyte.

One embodiment of the present invention is a meter 10 as shown in FIG. 1. The meter 10 has a display 12 that is adapted to display information to a user of the meter 10. Some of the information that may be displayed to a user includes concentration readings, time and date indicators, markers and alarms. The meter 10 also has at least one user input mechanism 15 that is adapted to allow the user to make selections relating to one or more user features. The user input mechanism 15 may include, for example, buttons, scroll bars, touch screens, or any combination of such items. The meter 10 may also have a memory device 17 that is adapted to store concentration readings, etc.

According to one embodiment of the present invention, the meter 10 includes a post-meal test-time alarm 18. This alarm 18 is adapted to remind a user to test his or her blood glucose concentration after a meal. Preferably, the alarm 18 reminds a user to test his or her blood glucose concentration about 1½ to about 2½ hours, and most desirably about 2 hours, after a meal. This length of time after a meal has been determined to be the most critical glucose monitoring time since it represents the time frame when blood glucose levels typically spike and can cause the most harm. While some meters provide the capability to program test-time alarms, the present invention automatically ties the alarm to a meal marker and provides for the alarm to go off after a predetermined amount of time. While the remainder of the disclosure herein will be directed towards post-meal test-time alarms associated with glucose meters, it is to be understood that the post-meal test-time alarm may be implemented in meters used for determining other analytes.

Turning in more detail to FIG. 1, the display 12 shows an analyte concentration reading 16. The reading 16 includes the numerical value and the appropriate units, i.e., 180 mg/dL. The display 12 also shows an icon representing a pre-meal marker 20 and an icon representing a post-meal test-time alarm 22. Also included on the display 12 is a time and date indicator 25. Other markers and/or features may be displayed on the display 12 in addition to the items described above.

To illustrate the use of the meter 10 and the post-meal test-time alarm 18 according to one embodiment, once a blood glucose concentration reading 16 is obtained, the meter 10 displays certain markers and/or user features. These features may be pre-programmed into the meter 10 before it is used by a user or the meter 10 may be customized for a particular user's needs after use begins. One of the items displayed is the pre-meal marker icon 20. In the example in FIG. 1, the pre-meal marker icon 20 is represented by the shape of an apple. Upon selection of this icon 20 by a user, the meter 10 automatically responds by flashing the post-meal test-time alarm icon 22. In the example in FIG. 1, the post-meal test-time alarm icon 22 is represented by the face of a clock. The user selects the post-meal test-time alarm icon 22 using the user input mechanism 15 to activate the post-meal test-time alarm 18. In addition to the icons described above, i.e., the apple and the clock, it is contemplated that other icons may be used as indicators of the pre-meal marker and the post-meal test-time alarm.

In some embodiments, the alarm 18 may produce a long beeping sound or shorter successive beeping sounds that occur about 2 to about 3 hours after the pre-meal marker is selected. Ideally, the alarm 18 is sounded about 2½ hours after the pre-meal marker is selected based on the assumption that the pre-meal reading is actually taken ½ hour before the meal so that the insulin has time to start working. Thus, a 2½ hour delay from the selection of the pre-meal marker activates the post-meal test-time alarm 18 which sounds about 2 hours after the user consumes a meal. If the user does not want to activate the post-meal test-time alarm 18, the user may make other selections via the input mechanism 15 and the post-meal test-time alarm icon 22 disappears from the display 12.

In addition to the pre-meal marker described above, others markers may be used to activate an alarm that is associated with certain events. Some examples of other markers (not shown) that may be used with the present invention are exercise markers, medication markers, fasting-time markers, log-book markers, and illness markers. The alarm can also be triggered after specific events such as a low or high concentration reading. For example, in one embodiment, an alarm can be triggered one hour after a low concentration reading. In another embodiment, the alarm can be triggered two hours after a high concentration reading. Additionally, the user can set an alarm to be triggered at a specific time each day, such as a noon-time alarm. While the use of the alarm is not tied to a specific event in that case, it reminds the user to take a concentration reading at a particular time each day.

Some commercially available meters, such as those that are manufactured and/or sold by Bayer Healthcare LLC of Tarrytown, N.Y., may be redesigned to incorporate the present invention, such as the Ascensia® CONTOUR® Blood Glucose Monitoring System and the Ascensia® BREEZE® Blood Glucose Monitoring System. It is contemplated that other meters, in addition to the ones listed above, may incorporate the present invention as described herein.

Alternative Embodiment A

A meter adapted to determine an analyte concentration reading, the meter comprising a display adapted to display information to a user of the meter, the display including information directed to a post-meal test-time alarm that is adapted to remind the user to obtain a post-meal analyte concentration reading, and at least one user input mechanism adapted to allow the user to activate the post-meal test-time alarm.

Alternative Embodiment B

The meter according to Alternative Embodiment A, further comprising a memory device adapted to store the analyte concentration reading.

Alternative Embodiment C

The meter according to Alternative Embodiment A, wherein the analyte is glucose.

Alternative Embodiment D

The meter according to Alternative Embodiment A, wherein the post-meal test-time alarm is adapted to remind the user to obtain the post-meal analyte concentration reading after a predetermined amount of time.

Alternative Embodiment E

The meter according to Alternative Embodiment D, wherein the post-meal test-time alarm is adapted to remind the user to obtain the post-meal analyte concentration reading about 1½ to about 2½ hours after a meal.

Alternative Embodiment F

The meter according to Alternative Embodiment E, wherein the post-meal test-time alarm is adapted to remind the user to obtain the post-meal analyte concentration reading about 2 hours after a meal.

Alternative Embodiment G

A method for using a meter adapted to determine an analyte concentration reading, the meter having a display adapted to display information to a user, the method comprising the acts of displaying information relating to a post-meal test-time alarm, activating the post-meal test-time alarm via an input mechanism, and sounding the post-meal test-time alarm after a predetermined amount of time to remind the user to obtain a post-meal analyte concentration reading.

Alternative Process H

The method according to Alternative Process G, further comprising storing the post-meal analyte concentration reading.

Alternative Process I

The method according to Alternative Process G, wherein the analyte is glucose.

Alternative Process J

The method according to Alternative Process G, wherein the sounding of the post-meal test-time alarm occurs about 1½ to about 2½ hours after a meal.

Alternative Process K

The method according to Alternative Process J, wherein the sounding of the post-meal test-time alarm occurs about two hours after a meal.

While the invention is susceptible to various modifications and alternative forms, specific embodiments and methods thereof have been shown by way of example in the drawing and are described in detail herein. Specifically, it is contemplated that many other markers may be used with the present invention to activate alarms in the same manner as described herein. It should be understood, however, that the description herein is not intended to limit the invention to the particular forms or methods disclosed, but, to the contrary, the intention is to cover all modifications, equivalents and alternatives falling within the spirit and scope of the invention as defined by the appended claims.

The invention claimed is:

1. A method for displaying information to a user, the method comprising:
    providing a device including a display and a memory device;
    displaying the analyte concentration reading on the display;
    displaying an icon representing a pre-meal marker on the display;
    in response to a selection of the icon representing a pre-meal marker being received by the device to mark that the analyte concentration displayed on the display is a pre-meal analyte concentration, displaying an icon representing a post-meal test-time alarm on the display; and
    in response to a selection of the icon representing a post-meal test-time alarm, automatically activating the post-meal test-time alarm after a predetermined amount of time to remind the user to obtain a post-meal analyte concentration reading, the predetermined amount of time being predetermined by the device.

2. The method according to claim 1, further comprising storing the post-meal analyte concentration reading in the memory device.

3. The method according to claim 1, wherein the analyte is glucose.

4. The method according to claim 1, wherein the predetermined amount of time is about 1½ to about 2½ hours from the selection of the icon representing a pre-meal marker.

5. The method according to claim 4, wherein the activating of the post-meal test-time alarm occurs about two hours after a meal.

6. The method of claim 1, wherein the icon representing a pre-meal marker is a food icon.

7. The method of claim 6, wherein the food icon is an apple.

8. The method of claim 1, wherein the icon representing a post-meal test-time alarm is a clock icon.

9. The method of claim 1, further comprising receiving, via a user input mechanism, a selection of the icon representing a pre-meal marker to mark the analyte concentration as a pre-meal analyte concentration.

10. The method of claim 1, wherein the device is a meter.

11. A method for displaying information to a user, the method comprising:
    providing a device including a display and a memory device;
    displaying the analyte concentration reading on the display;
    displaying an icon representing a pre-meal marker on the display;
    identifying the analyte concentration as a pre-meal analyte concentration reading via selection of the icon representing a pre-meal marker;
    in response to the identification of the pre-meal analyte concentration reading, displaying an icon representing a post-meal test-time alarm on the display; and
    in response to a selection of the icon representing a post-meal test-time alarm, activating the post-meal test-time alarm after a predetermined amount of time set by the device to remind the user to obtain a post-meal analyte concentration reading.

12. The method according to claim 11, further comprising storing the pre-meal analyte concentration reading and the post-meal analyte concentration reading in the memory device.

13. The method according to claim 11, wherein the analyte is glucose.

14. The method according to claim 11, wherein the predetermined amount of time is about 1½ to about 2½ hours from the selection of the pre-meal marker.

15. The method according to claim 14, wherein the activating the post-meal test-time alarm occurs about two hours after a meal.

16. The method of claim 11, wherein the icon representing a pre-meal marker is a food icon.

17. The method of claim 16, wherein the food icon is an apple.

18. The method of claim 11, wherein the icon representing a post-meal test-time alarm is a clock icon.

19. The method of claim 11, wherein the device is a meter.

* * * * *